(12) United States Patent
Rusin et al.

(10) Patent No.: US 6,437,019 B1
(45) Date of Patent: *Aug. 20, 2002

(54) GLASS IONOMER CEMENT

(75) Inventors: Richard P. Rusin, Woodbury; Joel D. Oxman, Minneapolis; Edward J. Winters, North St. Paul, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/571,780

(22) Filed: May 16, 2000

Related U.S. Application Data

(63) Continuation of application No. 08/663,963, filed on Jun. 14, 1996, now Pat. No. 6,136,885.

(51) Int. Cl.$^7$ .................................. A61K 6/08
(52) U.S. Cl. .................... 523/117; 524/30; 524/551; 524/555; 524/558; 524/815; 524/816; 524/829; 524/831; 524/833; 524/818; 524/494
(58) Field of Search .................. 523/116, 117; 524/30, 551, 555, 558, 815, 816, 829, 831, 832, 833, 818, 494

(56) References Cited

U.S. PATENT DOCUMENTS 5,367,002 A * 11/1994 Huang et al. ............... 523/116

* cited by examiner

*Primary Examiner*—Judy M. Reddick

(57) ABSTRACT

The present invention provides a multiple part ionomeric cement system comprising an organic composition that is substantially free of added water, and an aqueous composition comprising water. The organic composition contains at least a hydrophilic component and an acid functional compound that is provided as greater than 1.0% weight of the organic composition. The liquid ingredients of the compositions are miscible, both as separate compositions and when mixed together.

4 Claims, No Drawings

GLASS IONOMER CEMENT

This is a continuation of application Ser. No. 08/663,963 filed Jun. 14, 1996 now U.S. Pat. No. 6,136,885.

FIELD OF THE INVENTION

This invention relates to glass ionomer cement systems. More specifically, this invention relates to glass ionomer cement systems comprising an aqueous composition and an acidic organic composition.

BACKGROUND OF THE INVENTION

Glass ionomer cements in general are materials that comprise an ionic polymer composition and a reactive glass composition, where mixing these two compositions in an aqueous environment initiates a cement setting reaction. These materials are used in a number of applications in the dental and medical industries where a cement is used on, for example, tooth or bone structure. Conventionally, these materials are provided in two part systems, wherein one of the parts is in a powder form. Typically, the ionic polymer is provided in an aqueous liquid form and the reactive glass is provided as a powder. Considerable effort has been expended in designing systems to mix a powder and a liquid quickly and easily to enable complete reaction of conventional glass ionomer systems.

U.S. Pat. No. 4,288,355 to Anderson discloses surgical cement compositions comprising a concentrated non-gelling aqueous solution of a polycarboxylic acid and an aqueous suspension of metal oxide powder which when mixed together form a plastic mass which is formable into the desired shape before it hardens. These cements are formulated using a paste:paste format, but in all cases both pastes are aqueous pastes. This reference fails to disclose use of an organic paste for delivery of the reactive filler.

U.S. Pat. No. 4,591,384 to Akahane discloses dental cement compositions comprising a metal oxide and second ingredient capable of reacting with the metal oxide. The composition further comprises a tannic acid derivative that is sparingly soluble in water and a reducing agent that is soluble in water. Various forms of combining these two reactive ingredient are disclosed at column 2, lines 18–27. Included in this recitation is "powder/liquid, powder/paste, paste/paste, paste/liquid and the like," apparently indicating that all forms of delivery are equivalent for the cement system disclosed therein.

U.S. Pat. No. 5,063,257 to Akahane discloses dental glass ionomer cement compositions comprising (a) a polymer of an alpha-beta unsaturated carboxylic acid, (b) a fluoroaluminosilicate glass powder, (c) a polymerizable unsaturated organic compound, (d) a polymerization catalyst, (e) water, (f) a surfactant and (g) a reducing agent. Paste:paste compositions are exemplified having the ionomer in an aqueous paste and the reactive filler in an organic paste.

U.S. Pat. No. 5,154,762 to Mitra et. al discloses a Univeral Water-Based Medical and Dental Cement, wherein the cement contains water, acid-reactive filler, water-miscible acidic polymer, an ethylenically-unsaturated moiety, photoinitiator, water-soluble reducing agent and water-soluble oxidizing agent. Two-part paste:paste formulations are broadly disclosed at column 2, lines 58–66.

SUMMARY OF THE INVENTION

The present invention provides a multiple part ionomeric cement system comprising an organic composition that is substantially free of added water, and an aqueous composition comprising water. The organic composition contains at least a hydrophilic component and an acid functional compound that is provided as greater than 1.0% weight of the organic composition. The liquid ingredients of the organic composition form a miscible solution, and the liquid ingredients of the aqueous composition also form a miscible solution. The liquid ingredients of the organic composition and the aqueous composition when mixed together also form a miscible solution. At least one of the organic composition and the aqueous composition comprises an acid reactive filler, provided that the aqueous composition does not contain both an acid reactive filler and an acid. At least one of the organic composition and the aqueous composition comprises a polymerizable component. Al least one of the organic composition and the aqueous composition comprises a polymerization catalyst to initiate polymerization of said polymerizable component. Finally, the organic composition and the aqueous composition are substantially free of surfactant.

DETAILED DESCRIPTION OF PRESENTLY PREFERRED EMBODIMENTS

The present invention provides an easy to use glass ionomer cement system that has excellent strength characteristics as well as good wetting properties on a wet field in the oral environment. The system is surprisingly highly stable, because the acid component and the acid reactive filler component may be incorporated together in the organic composition without deleterious effects.

Because there is no surfactant in the composition and the liquid ingredients of each composition are miscible both before and after the parts are mixed, the instant compositions provide an excellent matrix when polymerized. Since the liquid ingredients form a single phase, the curative agents are uniformly dispersed throughout the matrix with no unpolymerized regions. The resulting compositions have excellent strength characteristics. Additionally, the compositions of the present invention exhibit excellent fluoride release.

Because the organic composition of the present invention is substantially free of added water, reactive filler may optionally be provided in both the organic and the aqueous compositions of the ionomeric cement. Higher reactive filler loading allows a better ionomeric matrix to be established upon curing, and a higher fluoride release may be achieved as well.

The liquid components of the aqueous and organic compositions of the present system are determined to be miscible by evaluation of the stability of the liquid components over time. The liquid components are placed mixed together in the desired ratio, and placed in a 25 mls vial such that the vial is about half full. The vial is then agitated by rotation around the short axis at about 25 revolutions per minute for three days. The vial is then allowed to stand for four weeks at ambient temperature and the presence of sediment is determined by visual inspection. If no sediment is observed, the composition is determined to be miscible and stable.

For purposes of the present invention, the term "substantially free of added water" means that the composition does not contain water that is intentionally added as a non-complexed or coordinated entity. It is understood that many materials, such as metals or glasses, contain water that is taken up from the atmosphere or is present as a coordination complex in its normal state. Water taken up by hygroscopic materials or present as a hydrate is permissibly present in the compositions described herein. Any water that is present in the composition, regardless of source, should not be present in amounts such that the water will have a deleterious effect on the long term properties of the composition. For example, water should not be present in an amount that would facilitate reaction of the fluoride-releasing material with the acidic component so that lumpiness or graininess of the material develops during commercially required storage times.

The compositions of the present invention are both liquid in nature, either as a readily flowable liquid or as a paste. Preferred ionomeric systems have both compositions provided as a paste. For purposes of the present invention, a paste is defined as a material wherein the inelastic modulus is less than the elastic modulus of the material. An organic paste is a paste wherein the liquid components are organic in nature, and wherein said organic paste is substantially free of added water. Preferably, the aqueous paste and the organic paste each have a viscosity between about $1 \times 10^2$ and $1 \times 10^{11}$ Cps. More preferably, the aqueous paste and the organic paste each have a viscosity between about $1 \times 10^7$ and $1 \times 10^9$ Cps. Viscosity is measured using a rheometer at a shear rate between 0.01 and 0.1 $\sec^{-1}$ at about 25° C. A preferred test protocol is to utilize a Bohlin CS50 controlled stress rheometer (Metric Group, Inc., Bohlin Instruments Division, Cranbury, N.J.) with 20 mm parallel plates and a gap of 2 mm. The stress is ramped from 1 Pascal up to a stress sufficient to reach a shear rate of approximately 0.1 $\sec^{-1}$.

The term "photocurable ionomer", as used herein, refers to a polymer having sufficient pendent ionic groups to undergo a setting reaction in the presence of a reactive filler and water, and sufficient pendent polymerizable groups to enable the resulting mixture to be polymerized, e.g., cured upon exposure to radiant energy. Alternatively, this ionomer may be cured by themal energy or exposure to a chemical redox catalyst system.

The term "reactive filler", as used herein, refers to a metal oxide or hydroxide, mineral silicate, or ion-leachable glass that is capable of reacting with an ionomer in the presence of water to form a hydrogel.

The term "non-reactive filler", as used herein, refers to filler materials that do not react with an ionomer in the presence of water to form a hydrogel.

The term "ionomer cement system", as used herein, refers to the unmixed, or mixed but unset and uncured, combination of ionomer, reactive filler, and other optional ingredients, such as water.

The term "working time", as used herein, refers to the time between the beginning of the setting reaction, i.e., when the ionomer and reactive filler are combined in the presence of water, and the time the setting reaction has proceeded to the point at which it is no longer practical to perform further physical work upon the system, e.g., spatulate it or reform it, for its intended dental or medical purpose.

The term "setting time", as used herein, refers to the time between the beginning of the setting reaction in a restoration, and the time sufficient hardening has occurred to allow subsequent clinical procedures to be performed on the surface of the restoration. Such hardening can occur either in the course of the normal setting reaction and/or by curing a photocurable system.

The organic composition, as described above, contains at a minimum a hydrophilic component and an acid functional compound. The hydrophilic component can be provided as a monomer, oligomer or polymer. Preferably, it is provided as either a linear homopolymer or copolymer, either of which may optionally be lightly crosslinked. The hydrophilic component is preferably miscible in water at concentrations of about 3% by weight or can absorb at least 2 g of water per hundred g of polymer. Optionally, the hydrophilic component can be a hydrophilic monomer which undergoes polymerization in situ leading to a hydrophilic, water-absorbing polymer. The hydrophilic monomer is preferably selected from the group consisting of 2-hydroxyethylmethacrylate or glycerol monomethacrylate, and mixtures thereof.

The acid functional compound may be any appropriate compound for glass ionomer reactions, provided that the compound selected meets the requirements of miscibility set forth elsewhere in this description. Preferred examples of such acids include organic mono or polyacidic compounds, such acrylic acid, methacrylic acid, itaconic acid, maleic acid, glutaconic acid, aconitic acid, citraconic acid, mesaconic acid, fumaric acid and tiglic acid.

Particularly preferred acidic compounds are the photo-curable ionomers that comprise a polymer having sufficient pendent ionic groups to undergo a setting reaction in the presence of a reactive filler and water, and sufficient pendent polymerizable groups to enable the resulting mixture to be cured by exposure to radiant energy.

Preferred photocurable ionomers have the general Formula I:

$$B(X)_m(Y)_n \qquad\qquad I$$

wherein

B represents an organic backbone, each X independently is an ionic group capable of undergoing a setting reaction in the presence of water and a reactive filler, each Y independently is a photocurable group, m is a number having an average value of 2 or more, and n is a number having an average value of 1 or more.

Preferably the backbone B is an oligomeric or polymeric backbone of carbon-carbon bonds, optionally containing non-interfering substituents such as oxygen, nitrogen or sulfur heteroatoms. The term "non-interfering" as used herein refers to substituents or linking groups that do not unduly interfere with either the photocuring reaction of the photocurable ionomer or its dark reaction with the reactive filler. Preferred X groups are acidic groups, with carboxyl groups being particularly preferred.

Suitable Y groups include, but are not limited to, polymerizable ethylenically unsaturated groups and polymerizable epoxy groups. Ethylenically unsaturated groups are preferred, especially those that can be polymerized by means of a free radical mechanism, examples of which are substituted and unsubstituted acrylates, methacrylates, alkenes and acrylamides. In aqueous systems, polymerizable groups that are polymerized by a cationic mechanism, e.g., polymerizable ethylenically unsaturated groups such as vinyl ether groups and polymerizable epoxy groups, are less preferred since a free radical mechanism is typically easier to employ in such systems than a cationic mechanism.

X and Y groups can be linked to the backbone B directly or by means of any non-interfering organic linking group, such as substituted or unsubstituted alkyl, alkoxyalkyl, aryl, aryloxyalkyl, alkoxyaryl, aralkyl, or alkaryl groups.

Photocurable ionomers of Formula I can be prepared according to a variety of synthetic routes, including, but not limited to, (1) reacting n X groups of a polymer of th[0085] formula $B(X)_{m+n}$ with a suitable compound in order to form n pendent Y groups, (2) reacting a polymer of the formula $B(X)_m$ at positions other than the X groups with a suitable compound in order to form n pendent Y groups, (3) reacting a polymer of the formula $B(Y)_{m+n}$ or $B(Y)_n$, either through Y groups or at other positions, with a suitable compound in order to form m pendent X groups and (4) copolymerizing appropriate monomers, e.g., a monomer containing one or more pendent X groups and a monomer containing one or more pendent Y groups.

The first synthetic route referred to above is preferred, i.e., the reaction of n X groups of a polymer of the formula $B(X)_{m+n}$, to form n pendent Y groups. Such groups can be reacted by the use of a "coupling compound", i.e., a compound containing both a Y group and a reactive group capable of reacting with the polymer through an X group in order to form a covalent bond between the coupling compound and the X group, thereby linking the Y group to the backbone B in a pendent fashion. Suitable coupling compounds are organic compounds, optionally containing non-interfering substituents and/or non-interfering linking groups between the Y group and the reactive group.

Particularly preferred photocurable ionomers of Formula I are those in which each X is a carboyl group and each Y is an ethylenically unsaturated group that can be polymerized by a free radical mechanism. Such ionomers are conveniently prepared by reacting a polyalkenoic acid (e.g., a polymer of formula $B(X)_{m+n}$ wherein each X is a carboxyl group) with a coupling compound containing both an ethylenically unsaturated group and a group capable of reacting with a carboxylic acid group. The molecular weight of the resultant photocurable ionomers is preferably between about 250 and about 500,000, and more preferably between about 5,000 and about 100,000. These ionomers are generally water-soluble but to a lesser extent than the polyalkenoic acids from which they are derived. Hence, the use of cosolvents, as described more fully below, is preferred in order to enhance the solubility of the ionomers and achieve more concentrated solutions thereof.

Suitable polyalkenoic acids for use in preparing ionomers of this invention include those homopolymers and copolymers of unsaturated mono-, di-, or tricarboxylic acids commonly used to prepare glass ionomer cements. Representative polyalkenoic acids are described, for example, in U.S. Pat. Nos. 3,655,605, 4,016,124, 4,089,830, 4,143,018, 4,342,677, 4,360,605 and 4,376,835.

Preferred polyalkenoic acids are those prepared by the homopolymerization and copolymerization of unsaturated aliphatic carboxylic acids, for example acrylic acid, 2-chloroacrylic acid, 3-chloroacrylic acid, 2-bromoacrylic acid, 3-bromoacrylic acid, methacrylic acid, itaconic acid, maleic acid, glutaconic acid, aconitic acid, citraconic acid, mesaconic acid, fumaric acid and tiglic acid. Suitable monomers that can be copolymerized with the unsaturated aliphatic carboxylic acids include unsaturated aliphatic compounds such as acrylamide, acrylonitrile, vinyl chloride, allyl chloride, vinyl acetate, and 2-hydroxyctliyl methacrylate. Ter-and higher polymers may be used if desired. Particularly preferred are the homopolymers and copolymers of acrylic acid. The polyalkenoic acid should be surgically acceptable, that is, it should be substantially free from unpolymerized monomers and other undesirable compositions.

Particularly preferred polyalkenoic acids also include homopolymers of polyacrylic acid, and copolymers of acrylic and itaconic acids, acrylic and maleic acids, methyl vinyl ether and maleic anhydride or maleic acid, ethylene and maleic anhydride or maleic acid, and styrene and maleic anhydride or maleic acid.

Polymers of formula $B(X)_{m+n}$ can be prepared by copolymerizing an appropriate mixture of monomers and/or comonomers. Preferably, such polymers are prepared by free radical polymerization, e.g., in solution, in an emulsion, or interfacially. Such polymers can be reacted with coupling compounds in the presence of appropriate catalysts.

Coupling compounds suitable for use for preparing the preferred ionomers of the present invention include compounds that contain at least one group capable of reacting with X in order to form a covalent bond, as well as at least one polymerizable ethylenically unsaturated group. When X is carboxyl, a number of groups are capable of reacting with X, including both electrophilic and nucleophilic groups. Examples of such groups include the following moieties, and groups containing these moieties: —OH, —NH$_2$, —NCO, —COCl, and

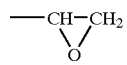

Examples of suitable coupling compounds include, but are not limited to, acryloyl chloride, methacryloyl chloride, vinyl azalactone, allyl isocyanate, 2-hydroxyethylmethacrylate, 2-aminoethylmethacrylate, and 2-isocyanatoethyl methacrylate. Other examples of suitable coupling compounds include those described in U.S. Pat. No. 4,035,321, the disclosure of which is hereby incorporated by reference. Examples of preferred coupling compounds include, but are not limited to, the following methacrylate compounds and their corresponding acrylates.

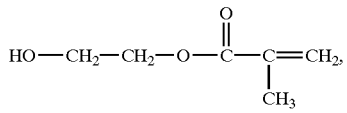

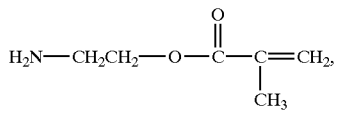

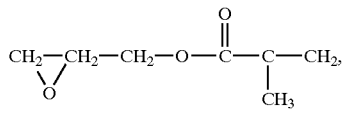

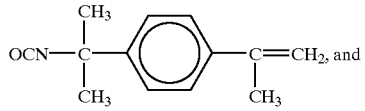

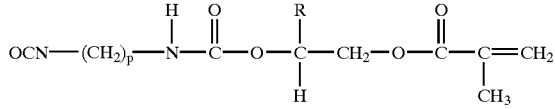

wherein p is 1 to 20 and R is H or lower alkyl (e.g., having 1 to 6 carbon atoms), as well as the following allyl compound

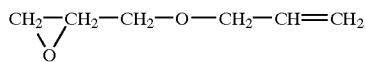

Particularly preferred coupling compounds are the following methacrylate compounds and their corresponding acrylates, wherein R is as defined above.

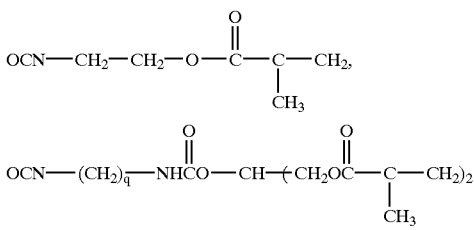

wherein q is 1 to 18.

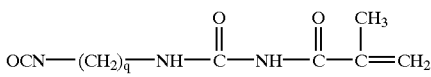

wherein q is as defined above.

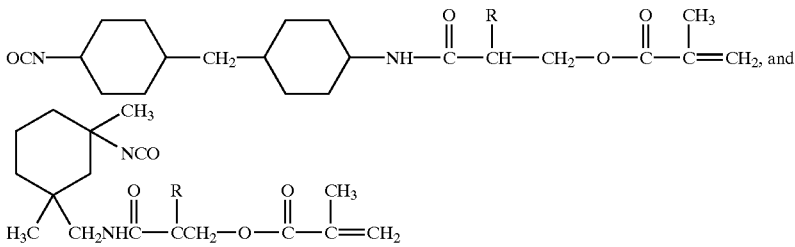

Preferred photocurable ionomers of Formula I are prepared by reacting a polymer of formula B(X)$_{m+n}$ wherein X is COOH with a coupling compound containing a reactive group of the formula NCO. The resultant ionomers, e.g., those of Formula I above wherein the covalent bond between the X group and the reactive group of the coupling compound is an amide linkage. These inomers provide an optimal combination of such properties as adhesion to dentin, mechanical strength, working time, fluoride release and the like.

The polymerizable components of the present compositions are compounds, which may be monomers, oligomers, or polymers, containing a polymerizable group. These polymerizable groups may be selected from free radically polymerizable groups, cationically polymerizable groups, or mixtures thereof. Preferably, the polymerizable compound has a molecular weight of between about 100 to 5000, and more preferably, has a molecular weight between about 200 and 1000. Mixtures of both higher and lower molecular weight polymerizable materials are also contemplated as providing special benefits in handling properties and ultimate cure material physical properties. In a preferred aspect of the present invention, at least some of the polymerizable material is relatively lower in viscosity than other ingredients of the composition so that it serves a viscosity lowering function in the overall uncured material. Preferably, at least some of the polymerizable material has a viscosity of less than 2000 cp, more preferably less than 500 cp, and most preferably less than 300 cp.

Reactive fillers suitable for use in the cement systems of this invention include those that are commonly used with ionomers to form ionomer cements. Examples of suitable reactive fillers include metal oxides such as zinc oxide and magnesium oxide, and ion-leachable glasses, e.g., as described in U.S. Pat. Nos. 3,655,605, 3,814,717, 4,143,018, 4,209,434, 4,360,605 and 4,376,835.

The reactive filler is preferably a finely divided reactive filler. The filler should be sufficiently finely-divided so that it can be conveniently mixed with the other ingredients and used in the mouth. Preferred average particle diameters for the filler are about 0.2 to about 15 micrometers, more preferably about 1 to 10 micrometers, as measured using, for example, a sedimentation analyzer.

Preferred reactive fillers are acid-reactive. Suitable acid-reactive fillers include metal oxides, metal salts and glasses. Preferred metal oxides include barium oxide, calcium oxide, magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosilicate glasses. Fluoroaluminosilicate glasses are particularly preferred. Suitable reactive fillers are also available from a variety of commercial sources familiar to those skilled in the art. For example, suitable fillers can be obtained from a number of commercially available glass ionomer cements, such as "GC Fuji LC" cement and "Kerr XR" ionomer cement. Mixtures of fillers can be used if desired.

If desired, the reactive filler can be subjected to a surface treatment. Suitable surface treatments include acid washing, treatment with phosphates, treatment with chelating agents such as tartaric acid, treatment with a silane or silanol coupling agent. Particularly preferred reactive fillers are silanol treated fluoroaluminosilicate glass fillers, as described in U.S. Pat. No. 5,332,429, the disclosure of which is expressly incorporated by reference herein.

The amount of reactive filler should be sufficient to provide a cement having desirable mixing and handling properties before cure and good cement performance after cure. Preferably, the reactive filler represents less than about 90%, more preferably about 25% to about 85%, and most preferably about 75% to about 85% by weight of the total weight of the organic paste compositions.

Non-reactive fillers may be selected from one or more of any material suitable for incorporation in compositions used for medical applications, such as fillers currently used in dental restorative compositions and the like. The filler is finely divided and preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or non-radiopaque.

Examples of suitable non-reactive inorganic fillers are naturally-occurring or synthetic materials such as quartz, nitrides (e.g., silicon nitride), glasses derived from, for example Ce, Sb, Sn, Zr, Sr, Ba and Al, colloidal silica, feldspar, borosilicate glass, kaolin, talc, titania, and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable non-reactive organic filler particles include filled or unfilled pulverized polycarbonates, polyepoxides, and the like. Preferred non-reactive filler particles are quartz, submicron silica, and non-vitreous microparticles of the type described in U.S. Pat. No. 4,503,169. Mixtures of these non-reactive fillers are also contemplated, as well as combination fillers made from organic and inorganic materials.

Preferably the surface of the filler particles is treated with a coupling agent in order to enhance the bond between the filler and the polymerizable resin. Suitable coupling agents include gamma-methacryloxypropyltrimethoxysilane, gamma-mercaptopropyltriethoxysilane, gamma-aminopropyltrimethoxysilane, and the like.

An additionally preferred filler is the class of bioactive glasses and glass-ceramics, which are believed to attach directly by chemical bonding to bone and other biological tissues. Examples of such materials are described in U.S. Pat. No. 5,074,916, which is incorporated herein by reference.

The ionomer cement system may utilize any of a number of modes of initiation of the polymerization reaction to initiate a crosslinking reaction. A preferred mode for initiation of the polymerization reaction is the incorporation of an oxidizing agent and a reducing agent as a redox catalyst system to enable the dental composition to cure via a redox reaction. Various redox systems and their use in ionomer cements are described in U.S. Pat. No. 5,154,762, the disclosure of which is expressly incorporated herein by reference.

The oxidizing agent should react with or otherwise cooperate with the reducing agent to produce free radicals capable of initiating polymerization of the ethylenically unsaturated moiety. The oxidizing agent and the reducing agent preferably are sufficiently shelf stable and free of undesirable coloration to permit their storage and use under typical dental conditions. The oxidizing agent and the reducing agent should also preferably be sufficiently soluble and present in an amount sufficient to permit an adequate free radical reaction rate. This can be evaluated by combining the ethylenically unsaturated moiety, the oxidizing agent and the reducing agent and observing whether or not a hardened mass is obtained.

Suitable oxidizing agents include persulfates such as sodium, potassium, ammonium and alkyl ammonium persulfates, benzoyl peroxide, hydroperoxides such is cumene hydroperoxide, tert-butyl hydroperoxide, tert-amyl hydroperoxide and 2,5-dihydroperoxy-2,5-dimethylhexane, salts of cobalt (III) and iron (III), perboric acid and its salts, salts of a permanganate anion, and combinations thereof Hydrogen peroxide can also be used, although it may, in some instances, interfere with the photoinitiator, if one is present. The oxidizing agent may optionally be provided in an encapsulated form as described in U.S. Pat. No. 5,154,762.

Preferred reducing agents include amines (and preferably aromatic amines), ascorbic acid, metal complexed ascorbic acid, cobalt (II) chloride, ferrous chloride, ferrous sulfate, hydrazine, hydroxylamine, oxalic acid, thiourea and salts of a dithionite, thiosulfate, benzene sulfinate, or sulfite anion.

The ionomer cement systems of the invention may contain one or more suitable photopolymerization initiators that act as a source of free radicals when activated. Such initiators can be used alone or in combination with one or more accelerators and/or sensitizers.

The photoinitator should be capable of promoting free radical crosslinking of the ethylenically unsaturated moiety on exposure to light of a suitable wavelength and intensity. It also preferably is sufficiently shelf stable and free of undesirable coloration to permit its storage and use under typical dental conditions. Visible light photoinitiators are preferred. The photoinitiator preferably is water soluble or water miscible. Photoinitiators bearing polar groups usually have a sufficient degree of water solubility or water miscibility. The photoinitiator frequently can be used alone, but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone. and a diaryliodonium salt, e.g., diphenyliodonium chloride, bromide, iodide or hexafluorophosphate, with or without additional hydrogen donors (such as sodium benzene sulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source, the thickness of the layer to be exposed to radiant energy, and the extinction coefficient of the photoinitiator. Typically, the photoinitiator compositions will be present at a total weight of about 0.01 to about 5%, more preferably from about 0.1 to about 5%, based on the total weight of the composition.

Having three cure mechanisms in the glass ionomer system (photocure, dark cure through a redox reaction, and ionic cure) facilitates thorough, uniform cure and retention of good clinical properties. Cements utilizing three modes of cure have particular utility in clinical applications where cure of a conventional light-curable composition may be difficult to achieve. Such applications include deep restorations, large crown build-ups, endodontic restorations, luting of metallic crowns or other light-impermeable prosthetic devices to teeth, and other restorative applications in inaccessible areas of the mouth.

For photocurable ionomers that are polymerized by a cationic mechanism, suitable initiators include salts that are capable of generating cations such as the diaryliodonium, triarylsulfonium and aryldiazonium salts.

Optional other ingredients, such as polymerization initiators, modifying agents and cosolvents can be added at any time and in any manner that does not prematurely begin the setting reaction or the photocuring reaction.

Modifying agents can be used in the ionomer cement systems of the present invention in order to provide prolonged working times. Modifying agents useful in the cement system of the present invention are, for example, alkanolamines, e.g., ethanolamine and triethanolamine, and mono-, di- and tri-sodium hydrogenphosphates. Modifying agents can be incorporated into either or both pastes of the present invention. The modifying agents are preferably used at a concentration between about 0.1 to about 10 percent by weight, based on the weight of the reactive filler, and preferably between about 0.5 to about 5 percent Cosolvents useful in the present invention include. but are not limited to, low molecular weight organic solvents. The word "cosolvent", as used herein refers to a material that aids in the dissolution of a photocurable ionomer in water, in order to form a homogeneous aqueous solution of cosolvent and ionomer.

Optionally, the glass ionomer cement may contain stabilizers. The incorporation of stabilizers serves to further improve the color stability of paste:paste compositions. Suitable stabilizers include oxalic acid, sodium metabisulfite, metaphosphoric acid, sodium bisulfite, sodium thiosulfate, and combinations thereof. Oxalic acid and sodium metabisulfite are preferred stabilizers.

If desired, the cements of the invention can contain adjuvants such as pigments, inhibitors, accelerators, viscosity modifiers, medicaments (including antimicrobial agents such as benzalkonium chloride, and glutaraldehyde, chlorhexidine gluconate) and other ingredients that will be apparent to those skilled in the art.

It has further surprisingly been found that addition of submicron silica particles (e.g., pyrogenic silicas such as the "Aerosil" Series "OX 50", "130", "150" and "200" silicas sold by Degussa and "Cab-O-Sil M5" silica sold by Cabot Corp.) to the organic paste substantially improves the handling properties of that paste.

The pastes of the photocurable ionomer cement system can be combined, e.g., blended or mixed, in a variety of manners and amounts in order to form the photocurable ionomer cement of this invention. Mixture by spatulation is an option, but the present formulation lends itself well to novel and advantageous delivery of glass ionomer systems using a multiple barrel syringe delivery system using a static mixing element to assure adequate mixing of the two pastes. Such a system is described in pending U.S. patent application Ser. No. 08/202,390, filed Feb. 28, 1994 U.S. Pat. No. 5,624,260 and in U.S. patent application Ser. No. 08/547, 451 filed, Oct. 24, 1995 U.S. Pat. No. 5,722,829.

Sufficient amounts of each composition in the cement systems of the present invention should be employed to obtain the desired working time. Preferably such systems will provide a working time of at least about one minute and most preferably greater than two minutes, during which time the systems can be cured by exposure to an appropriate source of radiant energy. For the sake of brevity this discussion will focus on dental applications, and particularly, the curing of such systems in situ, e.g., in the mouth of a patient.

The curing of the ionomer cement system is accomplished by exposure to any source of radiant energy capable of causing the desired extent of polymerization of the photocurable ionomer. Suitable radiant energy sources afford a desired combination of such properties as safety, controllability, suitable intensity, and suitable distribution of incident energy. See generally, "Radiation Curing", Kirk-Othmer Encyclopedia of Chemical Technology 3d Ed., Vol. 19, pp. 607–624 (1982). Preferred radiant energy sources are ultraviolet or visible light sources whose emission spectra correspond closely with the absorption range of the polymerization initiator in the ionomer cement system. For instance, sources emitting ultraviolet light at wavelengths between about 335 and 385 nm, and sources emitting visible light in the blue region at wavelengths between about 420 and 480 nm are preferred for use with the preferred ultraviolet- and visible-light-induced polymerization initiators, respectively. For polymerizing cement systems in the mouth, visible light radiation such as that provided by standard dental curing lights is particularly preferred.

Upon exposure of an ionomer cement system of the present invention to an appropriate source of radiant energy, the system rapidly begins to cure, e.g., within about 45 seconds, and preferably within about 30 seconds. The restoration generally exhibits the greatest degree of cure near its surface, where the radiant energy is most intense. The surface of the restoration therefore can be cured sufficiently to allow subsequent procedures to be performed on the restoration, while the interior of the restoration is allowed to harden fully by means of the ongoing setting reaction. Thus, if the curing step is[]omitted, the usual setting reaction will occur, ultimately resulting in the hardening of the material, even in the dark. This phenomenon offers a unique advantage in that a relatively deep restoration can be prepared by rapidly curing the outer surface of the restoration instantly by-exposure to radiant energy, allowing the inner portions of the restoration to cure more slowly by the usual setting reaction. As a result, the dentist can continue to carry out further restorative procedures, e.g., layering further ionomer cement on the hardened surface, while the inner portions continue to harden. This can result in a substantial saving of time for the practitioner and patient.

The ionomer cements of this invention can be used in a variety of applications in the dental or medical fields in which a bulk curable material of low shrinkage is desired that will adhere well to the surrounding tooth or bone structure. For instance, these cements can be used as dental restoratives, liners, bases, cements, sealants and as dental or orthodontic adhesives.

The present invention will be further understood in view of the following examples which are merely illustrative and not meant to limit the scope of the invention. Unless otherwise indicated, all parts and percentages are by weight, "glass" is the treated fluoroaluminosilicate glass of PREPARATORY EXAMPLE 1 and "OX 50" is the treated OX 50 of PREPARATORY EXAMPLE 2.

PREPARATORY EXAMPLE 1

Treated Fluoroaluminosilicate Glass

The ingredients set out below in TABLE I were mixed, melted in an arc furnace at about 1350–1450° C., poured from the furnace in a thin stream and quenched using chilled rollers to provide an amorphous single-phase fluoroaluminosilicate glass.

TABLE I

| Ingredient | Parts |
| --- | --- |
| $SiO_2$ | 37 |
| $AlF_3$ | 23 |
| $SrCO_3$ | 20 |
| $Al_2O_3$ | 10 |
| $Na_3AlF_6$ | 6 |
| $P_2O_5$ | 4 |

The glass was ball-milled to provide a pulverized frit with a surface area of 2.5–3.2 m²/g measured using the Brunauer, Emmet and Teller (BET) method.

A silanol solution was prepared by mixing together 2.4 parts gamma-methacryloxypropyl trimethoxysilane ("A-174", Union Carbide Corp.), 12.6 parts methanol, 36.5 parts water and 0.33 parts acetic acid. The mixture was stirred magnetically for 60 minutes at ambient temperature, added to 60.8 parts of the glass powder and slurried for 30 minutes at ambient temperature. The slurry was poured into a plastic-lined tray and dried for 10 hours at 80° C. The silanol treated dried powder was sieved through a 60 micrometer mesh screen.

PREPARATORY EXAMPLE 2

Treated OX 50 Silica

A-174 silane (3.7 g) was added with stirring to 50 g of deionized water acidified to pH 3–3.3 by dropwise addition of trifluoroacetic acid. The resultant mixture was stirred at about 25° C. for 1 hour at which time 95 g of OX 50 silica were added to the mixture with continued stirring for 4 hours. The slurry was poured into a plastic-lined tray and dried at 35° C. for 36 hours. The silanol treated dried powder was sieved through a 74 micrometer mesh screen.

PREPARATORY EXAMPLE 3

Treated Zinc Fluoroaluminosilicate Glass

The ingredients set out below in TABLE II were mixed, melted in an arc furnace at about 1350–1450° C., poured from the furnace in a thin stream and quenched using chilled rollers to provide a zinc fluoroaluminosilicate glass.

TABLE II

| Ingredient | Parts |
|---|---|
| $SiO_2$ | 27 |
| $AlF_3$ | 23 |
| SrO | 12.6 |
| $Al_2O_3$ | 0.8 |
| $Na_3AlF_6$ | 10.6 |
| $P_2O_5$ | 1 |
| ZnO | 21 |
| $B_2O_3$ | 2 |
| MgO | 2 |

The glass was ball-milled to provide a pulverized frit with a surface area of 2.5–3.2 m²/g measured using the Brunauer, Emmet and Teller (BET) method.

A silanol solution was prepared by mixing together 2.4 parts gamma-methacryloxypropyl trimethoxysilane ("A-174", Union Carbide Corp.), 12.6 parts methanol, 36.5 parts water and 0.33 parts acetic acid. The mixture was stirred magnetically for 60 minutes at ambient temperature, added to 60.8 parts of the glass powder and slurried for 30 minutes at ambient temperature. The slurry was poured into a plastic-lined tray and dried for 10 hours at 80° C. The silanol treated dried powder was sieved through a 74 micrometer mesh screen.

EXAMPLE 1

For each of the run nos. in TABLE III, the designated monomer was independently combined with either 5% of an ethylenically unsaturated acidic copolymer prepared like the precipitated dry polymer of EXAMPLE 11 of U.S. Pat. No. 5,130,347 ("CP") or 5% polyacrylic acid ("PAA"; molecular weight 2000; Aldrich). The ingredients of each run no. were weighed into a glass vial, mixed for 3 days using a twin shell dry blender (from Paterson-Kelley Company, East Stroudsburg, Pa.) allowed to stand undisturbed for 4 weeks and then the appearance was visually observed. "Clear solution" was noted for run nos. 1 and 4 in which no precipitate, undissolved matter, cloudiness or separation was observed; hence, these were clear solutions in which the ingredients were miscible and would be suitable solutions of the invention. "Sediment" was noted for run nos. 2–3 and 5–17 in which a precipitate, undissolved matter, cloudiness or separation was observed.

TABLE III

| Run No. | Monomer | CP | PAA |
|---|---|---|---|
| 1 | 2-Hydroxyethyl methacrylate | Clear Solution | Clear Solution |
| 2 | Hydroxypropyl methacrylate | Sediment | Sediment |
| 3 | Polyethylene glycol dimethacrylate, MW = 400[1] | Sediment | Sediment |
| 4 | Glycerol monomethacrylate | Clear Solution | Clear Solution |
| 5 | Polyethylene glycol monomethacrylate, MW = 400 | Sediment | Sediment |
| 6 | Polyethylene glycol monomethacrylate | Sediment | Sediment |
| 7 | Glycerol dimethacrylate | Sediment | Sediment |
| 8 | Methyl methacrylate | Sediment | Sediment |
| 9 | Ethyl methacrylate | Sediment | Sediment |
| 10 | 2-tert-Butylaminomethyl methacrylate | Sediment | Sediment |
| 11 | Tertahydrofurfuryl methacrylate | Sediment | Sediment |
| 12 | Ethyltriglycol monomethacrylate | Sediment | Sediment |
| 13 | 50% Bis-GMA[3], 50% TEGDMA[4] | Sediment | Sediment |

TABLE III-continued

| Run No. | Monomer | CP | PAA |
|---|---|---|---|
| 14 | Urethane dimethacrylate | Sediment | Sediment |
| 15 | Dimethylaminoethyl methacrylate | Sediment | Sediment |
| 16 | Methacrylic acid | Sediment | Sediment |
| 17 | Bis-EMA[5] | Sediment | Sediment |

[1]Polyethyleneglycol$_{400}$ dimethacrylate (Rohm-Tech, Malden MA).
[2]Glycerol monomethacrylate.
[3]2,2-Bis[4-(2-hydroxy-3-methylacryloxypropoxy)phenyl]propane.
[4]Triethyleneglycol dimethacrylate.
[5]Ethoxylated bisphenol A dimethacrylate (6 mole, Sartomer Company, Exton, PA).

EXAMPLE 2

The ingredients set out below in TABLE IV were independently combined to form six Organic Paste compositions designated OPa through OPf. The ingredients, except the glass and the OX 50 silica, were mixed together first; all formed clear, miscible solutions that showed no precipitates or liquid-liquid separation. Then the glass and OX 50 silica, where present, were admixed with the solution to form a paste. For OPf, 36.3 parts calcium phosphate were admixed with the solution to form a paste.

TABLE IV

| Organic Paste | Ingredients (Parts) | | | | | | |
|---|---|---|---|---|---|---|---|
| | HEMA[1] | CP[2] | PEG$_{400}$DMA | BPO[3] | BHT[4] | Glass[5] | OX-50[6] |
| a | 35 | 15 | — | 0.4 | 0.04 | 25 | — |
| b | 12.18 | 5.47 | 17.65 | 0.28 | 0.03 | 58 | 6.7 |
| c | 69 | 31 | — | 0.4 | 0.04 | 50 | — |
| d | 44.2 | 19.9 | — | 0.6 | 0.06 | — | 35.9 |
| e | 69 | 31 | — | 1.0 | 0.1 | — | — |
| f | 44.59 | 19.1 | — | 0.51 | 0.05 | — | — |

[1]2-Hydroxy ethylmethacrylate.
[2]Ethylenically unsaturated acidic copolymer prepared like the precipitated dry polymer of EXAMPLE 11 of U.S. Pat. No. 5,130,347.
[3]Benzoyl peroxide.
[4]Butylated hydroxytoluene.
[5]Glass of PREP. EX. 1.
[6]Fumed silica of PREP. EX. 2.

The ingredients set out below in TABLE V were independently combined to form fifteen Aqueous Paste compositions designated APa through APo. In a manner similar to that detailed for the formation of the organic pastes, each aqueous paste was formed by first admixing the ingredients other than the glass and the OX 50 silica; all formed clear, miscible solutions that showed no precipitates or liquid-liquid separation. Then the glass and OX 50 silica, where present, were added to the solution to form a paste. In addition to the ingredients listed in TABLE V, APi contained 29.0 parts HEMA, APk contained 0.02 parts BHT, API contained 2.5 parts glutaric dialdehyde, APm contained 17.5 parts PEG400 and APn contained 0.13 parts camphorquinone.

TABLE V

| Aqueous Paste | Ingredients (Parts) | | | | | | |
|---|---|---|---|---|---|---|---|
| | H$_2$O[1] | PEG$_{400}$DMA | CP | DMAPE[2] | TBA[3] | Glass | OX 50 Silica |
| a | 10.4 | 15.6 | — | 0.26 | — | 66 | 8 |
| b | 10.6 | — | — | — | 0.13 | 68.3 | 5 |
| c | 10.4 | — | — | — | 0.26 | 68 | 5.9 |
| d | 22.8 | 34.2 | — | — | 0.57 | — | 43 |
| e | 13.9 | — | — | 0.35 | — | 65.3 | — |
| f | 54.7 | — | 13.68 | 1.37 | — | — | 31.6 |
| g | 11.6 | 17.34 | — | — | — | 65.9 | 5.2 |
| h | 22.8 | 34.2 | — | 0.57 | — | — | 43 |
| i | 19.4 | — | — | 0.48 | — | — | 51.6 |
| j | 12 | 18 | — | 0.15 | — | 65 | 5 |
| k | 10.3 | 15.4 | — | — | 0.18 | 66.1 | 8.2 |

[1]Deionized water.
[2]Dimethylaminophenethanol.
[3]4-Tert-butyl-N,N-dimethylaniline.

The pastes set out below in TABLE VI were independently loaded into various types of containers and periodically checked for stability. "Syringes" were black polyethylene syringes of approximately 3 ml filled volume with 1 mm wall thickness and 8 mm inside diameter; "glass jars" were 250 ml glass jars with metal lids; "plastic jars" were polypropylene jars; and "Nalgene™ jars" were clear, high-density polyethylene containers from Nalge Company, Rochester, N.Y. At the time indicated in TABLE VI, the pastes in jars were probed with a plastic stick and the pastes in syringes were first dispensed in a pea-sized amount and then probed. If no polymerization or gelation of the cement was observed, the paste was considered stable. All the pastes were stable at the time periods indicated in TABLE VI.

TABLE VI

| Paste | Packaging | Time (Days) |
|---|---|---|
| APa | Syringe | 107 |
| APb | Syringe | 107 |
| OPa | Syringe | 107 |
| APc | Syringe | 107 |
| APd | Syringe | 107 |
| OPd | Glass Jar | 107 |
| APe | Glass Jar | 107 |
| APf | Glass Jar | 107 |
| APg | Plastic Jar | 107 |
| APh | Plastic Jar | 107 |
| OPc | Nalgene Jar | 300 |
| OPd | Glass Jar | 140 |
| OPe | Nalgene Jar | 140 |
| OPf | | |
| APi | Plastic Jar | 119 |
| APj | Glass Jar | 84 |
| APk | Plastic Jar | 119 |

What is claimed:

1. A multiple part ionomeric cement system comprising:
   a) an organic composition having a liquid ingredient, the composition being free of water, except as is present as a coordination complex in its normal state or that has been taken up from the atmosphere, comprising:
      i) a hydrophilic component, and
      ii) an acid functional polymer that comprises polymerizable functionality and is provided at greater than 1.0% by weight of the organic composition,
   wherein the liquid ingredient of said organic composition forms a miscible solution; and
   b) an aqueous composition whose liquid ingredients form a miscible solution; and
   when at least one of said organic composition and said aqueous composition comprises an acid reactive filler; said aqueous composition does not contain both an acid reactive filer and an acid; at least one of said organic composition and said aqueous composition comprises a polymerization catalyst to initiate polymerization of said polymerizable functionality; the liquid ingredients of said organic composition and said aqueous composition arc miscible when mixed together; and said organic composition and said aqueous composition are free of surfactant.

2. A multiple part ionomeric cement system comprising:
   a) an organic composition having a liquid ingredient, the composition being free of water, except as is present as a coordination complex in its normal state or that has been taken up from the atmosphere, comprising:
      i) a hydrophilic component, and
      ii) an acid functional compound that is a polymerizable component and is provided at greater than 1.0% by weight of the organic composition, wherein the acid functional compound is selected from the group consisting of acrylic acid, methacrylic acid, itaconic acid, maleic acid, glutaconic acid, aconitic acid, citraconic acid, mesaconic acid, fumaric acid and tiglic acid, and wherein the liquid ingredient of said organic composition forms a miscible solution, and
   b) an aqueous composition whose liquid ingredients form a miscible solution;
   and wherein at least one of said organic composition and said aqueous composition comprises an acid reactive filler; said aqueous composition does not contain both an acid reactive filler and an acid; at least one of said organic composition and said aqueous composition comprises a polymerization catalyst to initiate polymerization of said polymerizable component; the liquid ingredients of said organic composition and said aqueous composition are miscible when mixed together, and said organic composition and said aqueous composition are free of surfactant.

3. The system of claim 1, wherein said acid functional polymer is a polyalkenoic acid comprising polymerizable functionality.

4. The ionomeric cement system of claim 1, further comprising bioactive glass or glass-ceramic filler.

* * * * *

UNITED STATES PATENT AND TRADEMARK OFFICE
CERTIFICATE OF CORRECTION

PATENT NO.    : 6,437,019 B1
DATED         : August 20, 2002
INVENTOR(S)   : Rusin, Richard P.

It is certified that error appears in the above-identified patent and that said Letters Patent is hereby corrected as shown below:

Title Page,
Item [56], References Cited, U.S. PATENT DOCUMENTS, insert
-- 3,655,065   04/1972   Smith        260/29.6
   3,814,717   06/1974   Wilson       260/29.6
   4,016,124   08/1974   Crisp        260/29.6
   4,035,321   07/1977   Shahidi      260/22
   4,053,321   10/1977   Okumiya      106/57
   4,089,830   05/1978   Tezuka       260/29
   4,143,018   03/1979   Crisp        260/29.6
   4,209,434   06/1980   Wilson       260/29.6
   4,288,355   09/1981   Anderson     260/29.6
   4,342,677   08/1982   Muramatsu    523/116
   4,360,605   11/1982   Schmitt      523/116
   4,376,835   03/1983   Schmitt      523/116
   4,503,169   03/1985   Randklev     523/117
   4,591,384   05/1986   Akahane      106/35
   5,063,257   11/1991   Akahane      523/116
   5,074,916   12/1991   Hench        106/35
   5,130,347   07/1992   Mitra        522/149
   5,154,762   10/1992   Mitra        106/35
   5,189,077   02/1993   Kerby        523/116
   5,332,429   07/1994   Mitra        106/35
   5,367,002   11/1994   Huang        523/116
   5,453,456   09/1995   Mitra et al. 523/116
   5,520,725   05/1996   Kato et al.  523/116
   5,525,648   06/1996   Aasen et al. 523/116
   5,552,485   09/1996   Mitra et al. 525/102
   5,670,258   09/1997   Mitra et al. 428/405 --.
please insert
-- FOREIGN PATENT DOCUMENTS
WO    WO 95/22956   08/1995
WO    WO 89/10736   11/1989
EP    0 510 211     10/1992 --.
please insert
-- OTHER PUBLICATIONS
"Radiation Curing", Kirk-Othmer Encyclopedia of Chem. Tech. 3$^{rd}$ Ed., Vol. 19, pp. 607-624, (1982). --.

UNITED STATES PATENT AND TRADEMARK OFFICE
CERTIFICATE OF CORRECTION

PATENT NO. : 6,437,019 B1
DATED : August 20, 2002
INVENTOR(S) : Rusin, Richard P.

It is certified that error appears in the above-identified patent and that said Letters Patent is hereby corrected as shown below:

Column 1,
Line 43, delete "ingredient" and insert in place thereof -- ingredients --.

Column 2,
Line 15, delete "A1" and insert in place thereof -- At --.

Column 3,
Line 35, delete "themal" and insert in place thereof -- thermal --.

Column 4,
Line 16, insert -- as -- following "such".
Line 66, delete "th[0085]" and insert in place thereof -- the --.

Column 5,
Line 6, insert -- , -- preceding "and".
Line 22, delete "carboyl" and insert in place thereof -- carboxyl --.
Line 33, insert -- , -- preceding "but".
Line 34, delete "arc" and insert in place thereof -- are --.
Line 55, delete "hydroxyctlyl" and insert in place thereof -- hydroxyethyl --.
Line 56, delete "Ter-and" and insert in place thereof -- Ter-and --.

Column 7,
Lines 3□10, delete "
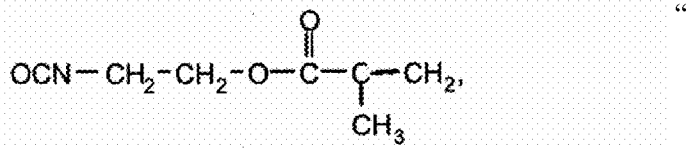

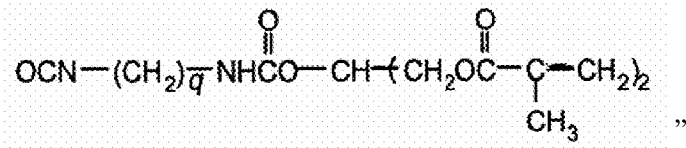
"

UNITED STATES PATENT AND TRADEMARK OFFICE
CERTIFICATE OF CORRECTION

PATENT NO. : 6,437,019 B1  Page 3 of 4
DATED : August 20, 2002
INVENTOR(S) : Rusin, Richard P.

It is certified that error appears in the above-identified patent and that said Letters Patent is hereby corrected as shown below:

Column 7 (cont'd),
And insert in place thereof --

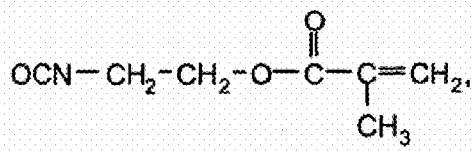

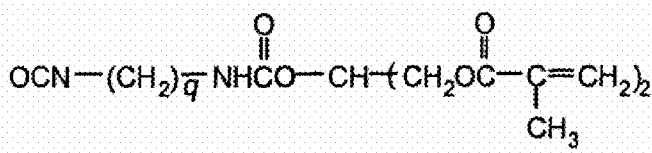

--.

Column 7,
Line 38, delete "inomers" and insert in place thereof -- ionomers --.

Column 9,
Line 57, insert -- . -- following "thereof".

Column 11,
Line 9, insert -- . -- following "percent".
Line 44, insert -- , -- following "1994".
Line 46, insert -- , -- following "1995".

Column 12,
Line 20, delete "[ ]" following "is".
Line 25, delete "-" preceding "exposure".
Line 46, before "ofPREPATORY" insert -- silica --.

Column 14,
Line 38, delete "precipate" and insert in place thereof -- precipitate --.

Column 15,
Line 10, insert -- . -- following "Maiden".
Line 24, insert -- . -- following "for".
Line 7, delete "EMA$^3$" and insert in place thereof -- EMA$^5$ --.
Line 54, delete "API" and insert in place thereof -- AP1 --.

UNITED STATES PATENT AND TRADEMARK OFFICE
CERTIFICATE OF CORRECTION

PATENT NO. : 6,437,019 B1
DATED : August 20, 2002
INVENTOR(S) : Rusin, Richard P.

It is certified that error appears in the above-identified patent and that said Letters Patent is hereby corrected as shown below:

Column 16,
Line 45, delete "," following "pastes".
Line 56, delete "OPd" and insert in place thereof -- OPb --.

Column 17,
Line 15, delete "when" and insert in place thereof -- wherein --.
Line 18, delete "filer" and insert in place thereof -- filler --.
Line 22, delete "arc" and insert in place thereof -- are --.

Signed and Sealed this

Sixteenth Day of March, 2004

JON W. DUDAS
*Acting Director of the United States Patent and Trademark Office*